United States Patent
Otsubo

(10) Patent No.: US 6,169,225 B1
(45) Date of Patent: Jan. 2, 2001

(54) DISPOSABLE TRAINING PANTS HAVING A SUSPENDED CROTCH COVERING SHEET

(75) Inventor: Toshifumi Otsubo, Kagawa-ken (JP)

(73) Assignee: Uni-Charm Corporation (JP)

( * ) Notice: Under 35 U.S.C. 154(b), the term of this patent shall be extended for 0 days.

(21) Appl. No.: 09/161,021

(22) Filed: Sep. 25, 1998

(30) Foreign Application Priority Data

Sep. 29, 1997 (JP) .................................................. 9-264656

(51) Int. Cl.[7] ............................. A61F 13/15; A61F 13/20
(52) U.S. Cl. ........................ 604/361; 604/378; 604/381; 604/385.01
(58) Field of Search ............................. 604/385.1, 385.2, 604/361, 381, 378

(56) References Cited

U.S. PATENT DOCUMENTS

| | | | |
|---|---|---|---|
| 5,342,343 | * | 8/1994 | Kitaoka et al. ................... 604/385.2 |
| 5,425,726 | * | 6/1995 | Shimizu et al. ................... 604/385.1 |
| 5,888,264 | * | 3/1999 | Matsushita ............................ 604/361 |
| 5,891,124 | * | 4/1999 | Nomura et al. ................... 604/385.1 |

FOREIGN PATENT DOCUMENTS

| | | | |
|---|---|---|---|
| 0661031 | * | 5/1995 | (EP) . |
| 7-33916 U | * | 6/1995 | (JP) . |

\* cited by examiner

Primary Examiner—John G. Weiss
Assistant Examiner—Michele Kidwell
(74) Attorney, Agent, or Firm—Baker & Daniels

(57) ABSTRACT

A disposable training pants include a basic structure wet telling means provided inside the basic structure. The basic structure include a pair of elastically stretchable/contractile suspender sheets extending circumferentially of front and rear waist regions of the basic structure, respectively, and an elastically stretchable/contractile crotch covering sheet secured at its longitudinally opposite ends to the respective suspender sheets at their middle portions so as to extend between the front and rear waist regions and serving to make a baby aware of wetness.

6 Claims, 3 Drawing Sheets

DISPOSABLE TRAINING PANTS HAVING A SUSPENDED CROTCH COVERING SHEET

BACKGROUND OF THE INVENTION

This invention relates to disposable training pants and more particularly to such pants useful to be put on a baby who should be trained so that the baby can smoothly proceed to a stage of life requiring no diaper.

Training pants of this type are well known, for example, from Japanese Utility Model Application Disclosure No. Hei7-33916, in which a wetness holding sheet is bonded along its longitudinally opposite ends to an inner surface of a pants laminate panel in its crotch region.

In the above-mentioned training pants, the wetness holding sheet does not extend longitudinally beyond the crotch region. A dimension of the wetness holding sheet as measured between its two fulcra at which the wetness holding sheet is bonded to the laminate panel is correspondingly small. Consequently, a degree of freedom for a relative movement between the wetness holding sheet and the laminate panel is too limited to stabilize the wetness holding sheet properly and satisfactorily in close contact with the baby's crotch and thereby to reliably make the baby aware of wetness.

SUMMARY OF THE INVENTION

In view of the above problem, it is an object of the invention to provide disposable training pants provided with wetness telling means adapted to satisfy requirements such that the degree of freedom is sufficiently high to stabilize the wetness telling means properly and satisfactorily in close contact with the baby's crotch and thereby to improve a wetness telling effect thereof.

According to the invention is provided an improvement in disposable training pants comprising a laminate panel composed of a liquid-permeable topsheet, a liquid-impermeable backsheet and a liquid-absorbent core disposed between these two sheets so as to define front and rear waist regions, a crotch region, a waist-opening and a pair of leg-openings, the openings being respectively provided with elastic members adapted to be stretchable/contractile circumferentially of the respective openings; and wetness telling means provided inside the laminate panel.

The improvement is characterized in that the wetness telling means comprise a pair of elastically stretchable/contractile suspender sheets respectively provided on an upper surface of the topsheet in the front and rear waist regions so as to extend circumferentially of the front and rear waist regions, each of the suspender sheets having upper and lower ends parallelly extending circumferentially of the associated one of the waist regions and transversely opposite side edges connecting these upper and lower ends to each other, and a crotch covering sheet secured at longitudinally opposite ends to the paired suspender sheets in the proximity of their middle portions; the wetness telling means are attached to the laminate panel by securing the upper ends of the paired suspender sheets to the laminate panel in the proximity of the front and rear upper ends of the waist-opening and securing the transversely opposite side edges of the paired suspender sheets to the laminate panel in the proximity of the transversely opposite side edges of the front and rear waist regions; and the crotch covering sheet has its transverse dimension insufficient to extend outward beyond the elastically stretchable/contractile members provided in association with the leg-openings.

DESCRIPTION OF THE PREFERRED EMBODIMENT

Specific modes in which the invention may be implemented will be described in details in reference with the accompanying drawings.

Figure 1:
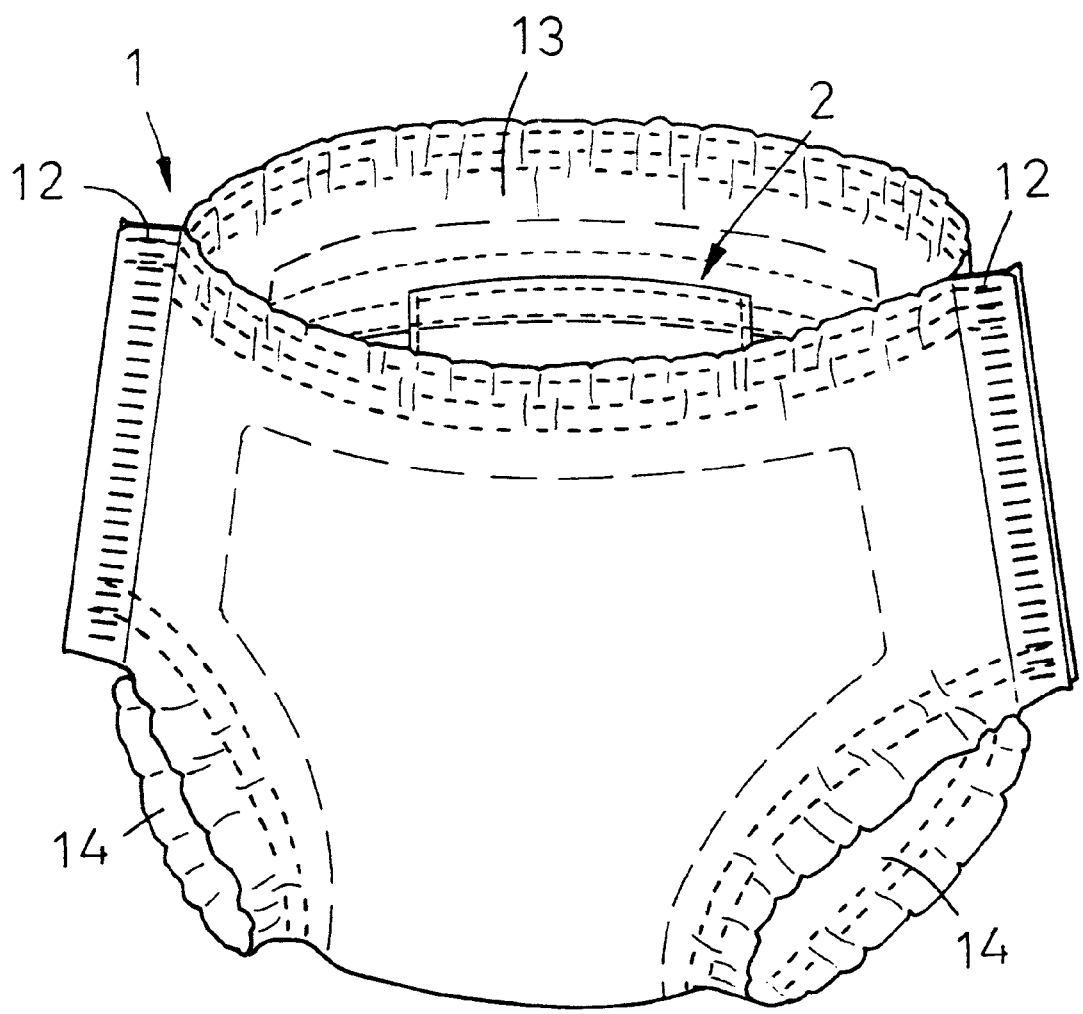
FIG. 1 is a perspective view of disposable training pants according to the invention.
Figure 2:
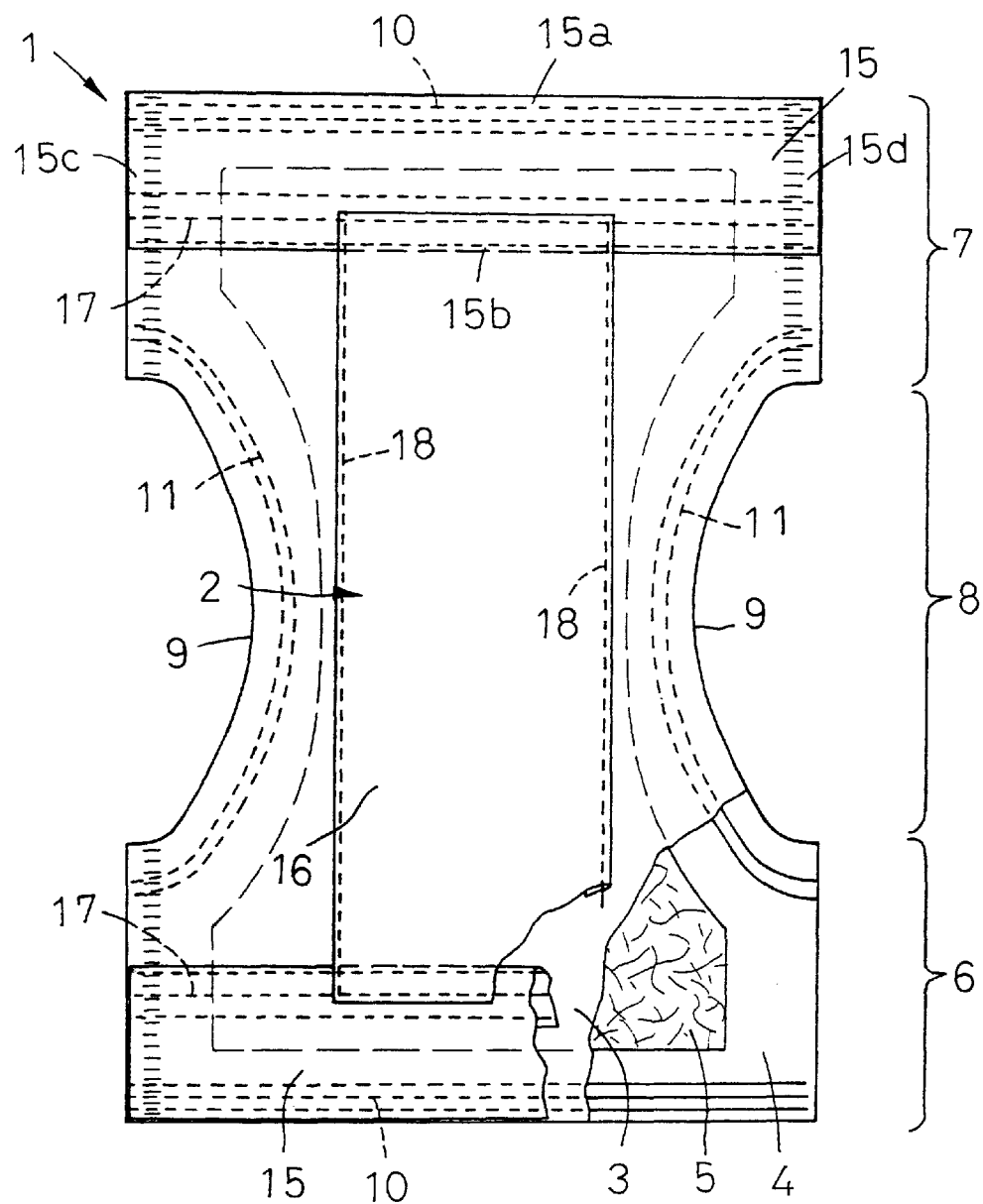
FIG. 2 is a plan view of an inner side of the partly cutaway pants as unfolded.
Figure 3:
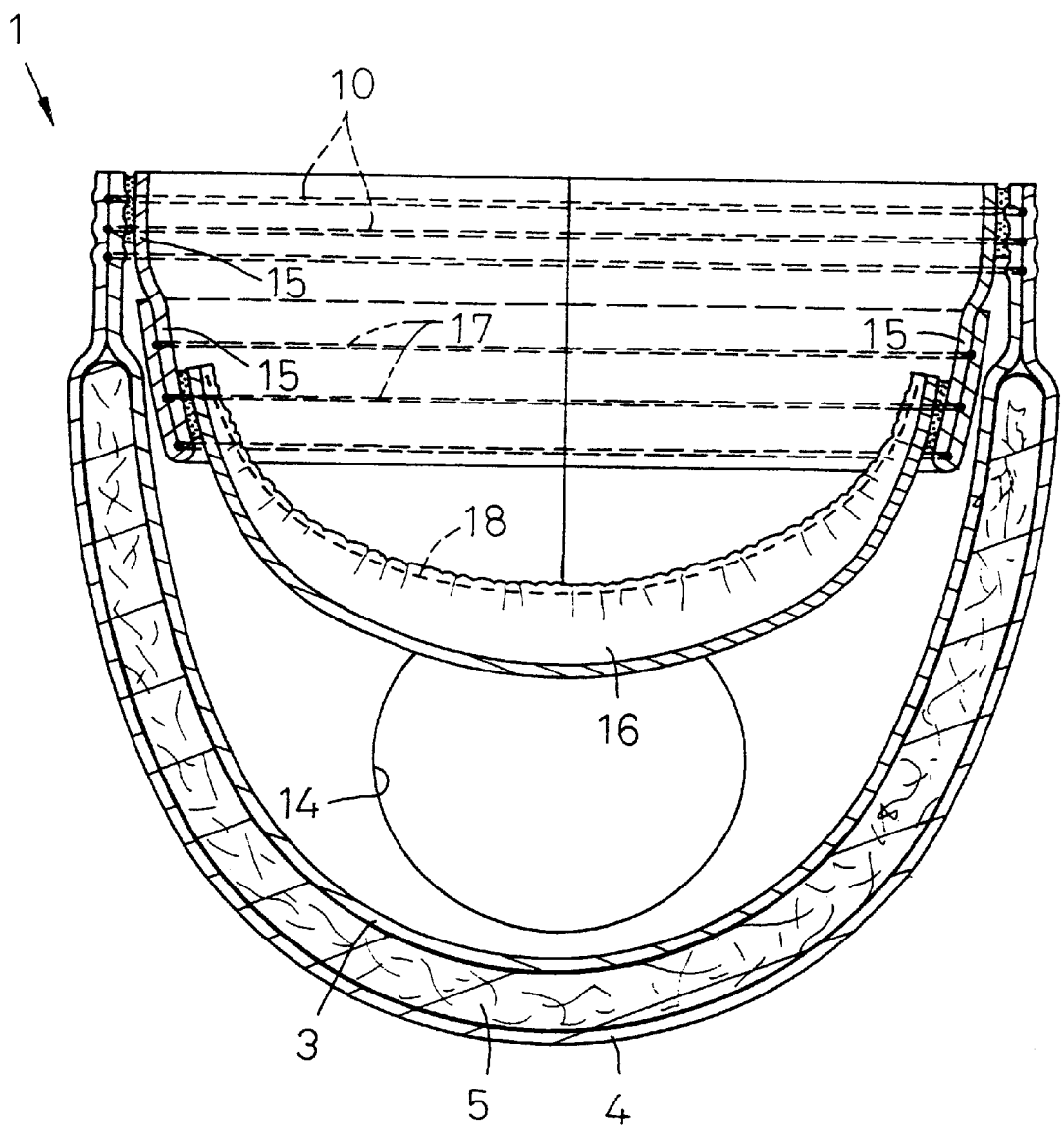
FIG. 3 is a sectional view of the pants taken along a longitudinal center line.

Referring to FIGS. 1–3, disposable pants according to the invention includes a laminate panel 1 and wetness telling means 2. The laminate panel 1 includes a liquid-permeable topsheet 3, a liquid-impermeable backsheet 4 and an hourglass-shaped liquid-absorbent core 5 disposed between the two sheets 3, 4. The laminate panel 1 assembled from these components defines a front waist region 6, a rear waist region 7 and a crotch region 8 extending between the front and rear waist regions 6, 7. The topsheet 3 and the backsheet 4 extend outward beyond peripheral edges of the core 5 longitudinally as well as transversely to define respective extensions and their transversely opposite side edges in the crotch region 8 describe concavely curved lines 9, 9. Longitudinally opposite extensions of the topsheet 3 and the backsheet 4 contain therebetween elastically stretchable/contractile members 10, 10 circumferentially acting upon the front and rear waist regions 6, 7 in a circumferential direction. Transversely opposite extensions of the topsheet 3 and the backsheet 4 contain therebetween elastically stretchable/contractile members 11, 11 acting thereupon along the concavely curved lines 9, 9, respectively. The elastically stretchable/contractile members 10, 10, 11, 11 are secured to the respective extensions under appropriate tension longitudinally of these members 10, 10, 11, 11. The laminate panel 1 is folded in two along a transverse center line extending across the crotch region 8 with the topsheet 3 lying inside the laminate panel 1. The front and rear waist regions 6, 7 are then intermittently bonded together along transversely opposite side edges 12, 12 of these front and rear waist regions 6, 7 by means of heat-sealing so as to define a waist-opening 13 and a pair of leg-openings 14, 14.

Construction of the laminate panel is well known and materials for the respective components are also well known. Fundamentally, it is essential for the laminate panel 1 assembled with the wetness telling means only to have the construction as has been described hereinabove. Additional arrangements and/or components are not important for the invention.

The wetness telling means 2 include a pair of suspender sheets 15, 15 and a crotch covering sheet 16. Each of the suspender sheets 15, 15 has upper and lower ends 15a, 15b extending circumferentially around the waist regions and transversely opposite side edges 15c, 15d connecting the upper and lower ends 15a, 15b to each other. The respective suspender sheets 15, 15 are provided in the form of rectangular strips narrower than the front and rear waist regions 6, 7, respectively. These paired suspender sheets 15, 15 are secured to the front and rear waist regions 6, 7 with their upper ends 15a, 15a to upper ends of the waist-opening 13 defined on the sides of the front and rear waist regions 6, 7, respectively and with their transversely opposite side edges 15c, 15d to the transversely opposite side edges of the front and rear waist regions 6, 7, respectively. The respective lower ends 15b, 15b are left free. There are provided a plurality of elastically stretchable/contractile members 17 in the proximity of the respective lower free ends 15b, 15b so that these members 17 may act upon the suspender sheets 15, 15 circumferentially of the waist regions, respectively. The crotch covering sheet 16 has a width smaller than a dimension by which the elastically stretchable members 11, 11 associated with the respective leg-openings 14, 14 are spaced from each other. The crotch covering member 16 extends between the paired suspender sheets 15, 15 and are secured to middle portions of the respective suspender sheets 15, 15 in the proximity of their lower free ends 15b, 15b. The crotch covering member 16 is provided along its transversely opposite side edges with elastically stretchable/ contractile members 18, 18 adapted to act thereupon along these side edges.

The crotch covering member 16 may be made of a sheet which can absorb and hold a quantity of urine discharged thereon, for example, a hydrophilic fibrous sheet or a foamed plastic sheet having open cells. Inversely, it is also possible to form the crotch covering sheet 16 using a hydrophobic fibrous sheet or a foamed plastic sheet having closed cells which are urine-unabsorbent but substantially urine-impermeable. In fact, it is not important whether the crotch covering sheet 16 should be made of hydrophilic material or hydrophobic material so far as an adequate quantity of urine stays on the crotch covering sheet 16 in contact with the baby's skin make the baby aware of wetness. Such material will be easily prepared by those skilled in the art.

In the disposable training pants according to the invention, a dimension of the crotch covering sheet extending between front and rear fulcra as measured longitudinally of the laminate panel is relatively large. This is achieved by the unique arrangement as follows: The suspender sheets as the components of the wetness telling means are secured in the proximity of their upper ends and transversely opposite side edges to the laminate panel in the proximity of the upper ends and the transversely opposite side edges of the front and rear waist regions. The crotch covering sheet forming the most important component of the wetness telling means is suspended from the lower free ends of the paired suspender sheets along which the crotch covering sheet is secured to the respective suspender sheets. In contrast with the conventional training pants in which the front and rear fulcra for the crotch covering sheet lie in the crotch region, a higher degree of freedom is ensured for a relative movement between the crotch covering sheet and the laminate panel. This means that the crotch covering sheet is properly and satisfactorily stabilized in close contact with the baby's crotch while the crotch covering sheet is, at least principally, suspended in midair. Accordingly, even if any external force moves the laminate panel relatively to the baby's body, the crotch covering sheet can be maintained in the close contact and reliably make the baby aware of wetness without being affected by the movement of the laminate panel.

The paired suspender sheets secured to the laminate panel in the proximity of the waist-opening have the elastically stretchable members provided independently of the elastically stretchable members associated with the laminate panel. These elastically stretchable members of the suspender sheets allow the suspender sheets to suspend the crotch covering sheet so as to be elastically kept in close contact with lower portions of the baby's trunk. In this manner, the paired suspender sheets are very effective to stabilize the crotch covering sheet relatively to the baby's crotch and thereby to prevent the crotch covering sheet from being easily displaced from its proper position.

What is claimed is:

1. Disposable training pants comprising:
   a liquid-permeable topsheet;
   a liquid-impermeable backsheet;
   a liquid-absorbent core disposed between the liquid-permeable topsheet and the liquid impermeable backsheet, said liquid-permeable topsheet, liquid-impermeable backsheet, and liquid absorbent core defining front and rear waist regions, a crotch region, a waist-opening and a pair of leg-openings;
   elastic members provided at said waist-opening and said leg-openings, said elastic members being stretchable/contractile circumferentially of the leg-openings and waist-openings; and
   wetness sensing means comprising:
   a pair of suspender sheets which are stretchable/contractile circumferentially of the front and rear waist regions and narrower than each of the front and waist regions in a longitudinal direction of the training pants, said suspender sheet being respectively provided on an upper surface of said topsheet in said front and rear waist regions so as to extend circumferentially along the front and rear waist regions, each of said suspender sheets having upper and lower ends parallelly extending circumferentially along respective ones of said waist regions and having transversely opposite side edges connecting said upper and lower ends to each other; and
   a crotch covering sheet secured at longitudinally opposite ends thereof to said pair of suspender sheets in the proximity of middle portions thereof, said crotch covering sheet being elastically stretchable/contractile in the longitudinal direction of the training pants and suspended by said pair of suspender sheets so as to be spaced apart from the topsheet,
   said upper ends of said paired suspender sheets being secured in the proximity of the front and rear upper ends of said waist-opening and said transversely opposite side edges of said paired suspender sheets being secured in the proximity of the transversely opposite side edges of said front and rear waist region, and
   said crotch covering sheet having a transverse dimension which is insufficient to extend outward beyond said elastically stretchable/contractile members provided at said leg-openings.

2. The disposable training pants according to claim 1, wherein said paired suspender sheets are made elastically stretchable/contractile by providing them with elastically stretchable/contractile members adapted to act circumferentially along said front and rear waist regions, respectively.

3. The disposable training pants according to claim 1, wherein said crotch covering sheet is elastically stretchable/contractile.

4. The disposable training pants according to claim 3, wherein said crotch covering sheet is made elastically stretchable/contractile by providing it at least along transversely opposite side edges thereof with elastically stretchable/contractile members.

5. The disposable training pants according to claim 1, wherein said crotch covering sheet is hydrophilic.

6. The disposable training pants according to claim 1, wherein said crotch covering sheet is hydrophobic and substantially liquid-impermeable.

\* \* \* \* \*